United States Patent [19]

Lund et al.

[11] Patent Number: 4,808,342

[45] Date of Patent: Feb. 28, 1989

[54] PRODUCTION OF SULFONATED AMINES

[75] Inventors: Richard B. Lund, Jackson; Milo C. Pass, Saraland, both of Ala.

[73] Assignee: Ciba-Geigy Corporation, Ardsley, N.Y.

[21] Appl. No.: 849,619

[22] Filed: Apr. 9, 1986

[51] Int. Cl.$^4$ .......................................... C07D 143/58
[52] U.S. Cl. .................................... 260/508; 260/509
[58] Field of Search ............................... 260/508, 509

[56] References Cited

PUBLICATIONS

Alexander, JACS, 69, 1599 (1947).
Tetrahedron Letters No. (43) pp. 4507–4510 (1968).
Collection Czechoslov. Chem. Commun. vol. 33, 2502–12 (1968).
Liebigs Annalen der Chemie 100, pp. 163–164 (1856).

Primary Examiner—Nicky Chan
Attorney, Agent, or Firm—Kevin T. Mansfield; Edward McC. Roberts

[57] ABSTRACT

A process for the preparation of sulfonated aromatic amines is disclosed based upon starting with the corresponding amine reacted with sulfuric acid in the presence of a sufficient excess of sulfuric acid to act as the reaction solvent. The sulfuric acid excess in the case of sulfanilic acid, the most common of these sulfonated amines and exemplified herein is an aniline:sulfuric acid ratio in the range 1:2.0 to 1:2.5. The reaction, with recycling of the excess acid, provides substantially 100% yield of high quality sulfonated aromatic amine with effectively no effluent but the product.

6 Claims, 4 Drawing Sheets

LAB-SCALE BATCH REACTOR

FIG. 2 LAB-SCALE CONTINUOUS REACTOR

FIG.3 CONTINUOUS MODE-PLANT SCALE

BATCH MODE-PLANT SCALE

PRODUCTION OF SULFONATED AMINES

FIELD OF THE INVENTION

This invention relates to the economic production of sulfonated aromatic amines and more particularly to the direct production of such sulfonated amines in a reaction medium consisting of concentrated sulfuric acid, one of the reactants.

BACKGROUND OF THE INVENTION

The sulfonated amines of the invention have the formula-

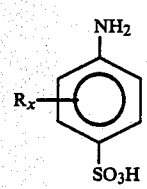

where R is H, $CH_3$, $C_2H_5$, halogen or

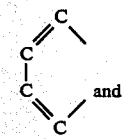

x is the integer 0 to 2 and are economically important as intermediates in the manufacture of such varied products ranging from dyestuffs to sulfa drugs.

The more commonly used and thus economically important sulfonated amines are those derived from aniline, the toluidines, xylidines, chloroanilines, naphthylamines, aminoanthraquinones and the like.

The simplest of the sulfonated aromatic amines is sulfanilic acid of the formula:

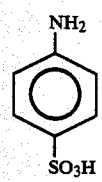

Large amounts of sulfanilic acid are consumed annually, primarily to produce dyestuffs but some is also used in the synthesis of other materials including substantial amounts of phenylhydrazine-p-sulfonic acid.

Upon diazotization, diazobenzene sulfonic acid is formed. This is an important intermediate in the dyestuff industry.

The major portion of the sulfanilic acid is consumed in the manufacture of fluorescent whitening agents. Such fluorescent dyestuffs are applied to paper, woven and non-woven textiles, and are components of soap and detergent laundering agents. Such fluorescent whitening agents are marketed under the Tinopal trademark. For example, major amounts are used for the manufacture of one of the whiteners applied to paper. Thus, any savings effected in the production of sulfanilic acid are of major economic interest.

The most straight forward synthesis of these amines and particularly sulfanilic acid consists of reacting the amine, aniline, with sulfuric acid in substantially stoichiometric proportions to form aniline hydrogen sulfate (AHS), followed by splitting off water and the migration rearrangement of the resulting sulfonic acid group to the para position according to the following equations:

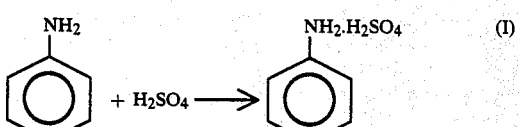

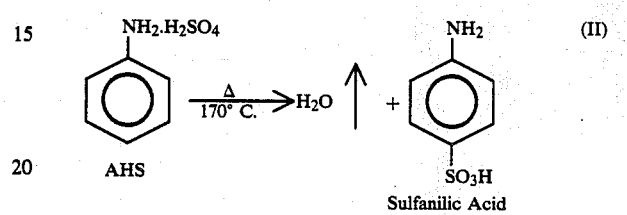

These reactions have been carried out directly or in the presence of inert, high boiling, water-immiscible solvents (Jacobs: *Ind. Eng. Chem.* 35; pg. 321–323).

The synthesis using such solvents produce a product of good appearance (Gardner color of 17 wt % solution of sodium salt <9) but solvent cost, handling, removal and recycling impose excessive costs that are not competitively bearable. Thus most sulfanilic acid until now was prepared in the absence of solvents.

The reaction (I) between aniline and sulfuric acid to form the aniline hydrogen sulfate proceeds as rapidly as the reactants are mixed and is exothermic. The heat of the exothermic reaction causes the temperature of the reaction mass to rise. Aniline hydrogen sulfate melts at about 160° C. It is very soluble in water at elevated temperatures. The temperature at which it liquifies varies with the amount of water in the mixture.

To cause water to be split off and to promote the para-rearrangement of reaction (II) at a slow but measurable rate, the minimum temperature must be about 165° C.–170° C. At this temperature, the aniline hydrogen sulfate is slowly converted, by an endothermic reaction, to sulfanilic acid. Sulfanilic acid, (in contrast to the aniline hydrogen sulfate salt) is stable and does not melt up to its decomposition temperature which is about 280° C.

It is instructive to visually observe the solventless conversion to sulfanilic acid of a molten mass of aniline hydrogen sulfate. As stated above, when water is present in the aniline hydrogen sulfate, the mixture forms a liquid or pasty mass at temperatures below 160° C. As the mass is heated, water is driven off so that substantially none is present at about 160° C.

When the temperature is raised to the rearrangement temperature, the conversion starts.

Sulfanilic acid is insoluble in molten aniline hydrogen sulfate. During the early stages of the conversion the molten mass becomes a pasty, sticky mass of a liquid phase and a dispersed solid phase. Bubbles form in the liquid from the water vapor that evolves. As the conversion continues, the mass becomes increasingly solid with a liquid phase dispersed within it. The upper surface is no longer smooth. It assumes a pockmarked appearance from the simultaneous escape of water vapor and the solidification of that part of the mixture from which it has emerged.

By maintaining the sample above the conversion temperature for a sufficient period of time, the sample is substantially completely converted to a block of solid sulfanilic acid which strongly adheres to the surface with which it was in contact during the conversion. It is this behavior pattern of the mixture during its conversion that has led to the previously employed dry processes briefly described below.

During this period of dry rearrangement and water elimination, color bodies of indeterminate composition form; causing a grayish or deep purplish product (Gardner color of 17 wt % solution of 8–9). For many uses this product, if not too intensely colored, can be used without further upgrading. It is known that iron tends to catalyze a reaction which also forms color bodies in the product.

In the dry processes, aniline and sulfuric acid, in substantially equimolar amounts are charged to the reactor to form aniline hydrogen sulfate therein. When the charging is completed, the temperature within the surrounding furnace is raised to heat the reactor and its contents above the rearrangement temperature. The released water is vented and is externally condensed.

Dry rod mill reactors and the tunnel kiln processes commonly used, are basically batch processes. The reactors have to be heated and then cooled. Heat transfer through the solid and semi-solid phases is poor. Rod mill reactors also serve as a mill to break up the lumps and break off the scale, thereby promoting the production cycle.

Other non-solvent "dry" processes include forming a pool of molten aniline hydrogen sulfate in which a segment of a continuously rotating drum dryer is immersed. The interior of the dryer is heated by high pressure steam or some other heat transfer fluid. The aniline hydrogen sulfate adhering to the exterior surface of the drum, after it emerges from the pool, is thus heated above the rearrangement temperature. The speed of rotation of the drum and the temperature to which the adherent film is raised are correlated so that rearrangement to sulfanilic acid is complete and the product removed before reentry of the drum portion into the molten pool. While feasible, the parameters of temperature, rotation rate, product adherence, separation, etc., render production control difficult so that this process is not economically viable.

Another "dry" method is based on mixing sulfuric acid, aniline and a small amount of water at about 125°–145° C. and spraying the resulting solution into a spray dryer along with air heated to about 400° C. The temperature of the outgoing air is held at about 260°–270° C. The resulting air stream, in which solid sulfanilic acid particles are entrained, is passed through a cyclone and bag filters. This separates the air from the solids. This method requires completion of the rearrangement in a very short period—in the order of a second. Current environmental requirements are very stringent and to meet even minimal solid separation requirements of the solid product from the gases necessitates inordinately expensive arrangements and investments.

Another "dry" variant involves utilization of fluidized bed technology wherein either solid or molten aniline hydrogen sulfate is continuously fed to a fluidized bed of sulfanilic acid. The bed is fluidized by a sufficiently hot inert gas to maintain the bed above the rearrangement temperature. The water vapor, which evolves, leaves carried by the vented inert fluidizing gas. Sulfanilic acid is continuously or periodically withdrawn from the reaction bed. The inert gas, which may be heated air at about 200° C.–250° C., is not only used as a fluidizing medium but also as the heating element and the carrier for sweeping out the water. Of course, this method requires very efficient cyclones and/or bag filters and often porous metal filters fitted with cyclic filter cleansing means to remove the product from the vented gases. These are expensive so that this method is non-competitive with the batch rod mill method.

All the above dry processes produce sulfanilic acid and/or aromatic amine p-sulfonates of considerable color. These colored products usually need purification to remove the undesirable colored intermediates which affect the purity of further products prepared therewith. The steps of decolorization by carbon absorption and other expedients raise the final cost of these important intermediates, particularly sulfanilic acid.

It is an object of this invention to prepare the above described sulfonated amine, at reasonable cost, at high purity and in good yield.

It is among further objects to provide a process for making such sulfonated amines of good color (about Gardner 1.0) by a process which is ecologically viable.

It is also an object to provide a process which permits a complete recycle of initially unutilized reactants- thus no effluent is produced and all the available energy produced by the reaction steps is absorbed in forwarding the reaction.

Another object is to provide for the preparation of the sulfonated amine, sulfanilic acid, of excellent color and at competitive costs by eliminating costly decolorizaiton steps.

THE INVENTION

The process of this invention is based on the preparation of sulfonated amines of the formula:

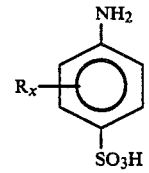

where R is H, CH$_3$, C$_2$H$_5$, halogen or

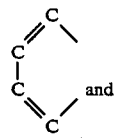

x is the integer 0 to 2: which comprises the steps treating an amine of the formula-

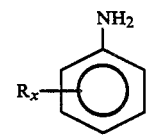

where $R_x$ is as indicated above with sulfuric acid to form the intermediate aromatic amine sulfate of the formula-

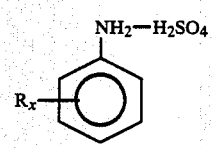

then heating this amine sulfate to cause rearrangement thereof and the formation of a sulfonate group with the elimination of a mole of water and the orientation of said sulfonate group to a position para or ortho to the restored amine group; wherein sulfuric acid is present in an excess sufficient to act as the reaction solvent and medium for the sulfate formation and rearrangement reaction; said sulfuric acid excess being equilibrated in amount and concentration so that the exotherm of reaction of the amine with the sulfuric acid will maintain the temperature of the reaction mixture between the rearrangement temperature for the amine sulfate and the decomposition temperature of said amine sulfonate for a time sufficient to substantially forward the rearrangement reaction and to distill off the water formed during sulfonate formation; distilling and collecting the formed water from said reaction mixture; and upon completion of the distillation, cooling the reaction mixture below the rearrangement temperatures for said amine sulfonate. The amine sulfonate can be harvested from the cooled reaction mixture by diluting the cooled mixture, as the amine sulfonates are only sparingly soluble in dilute sulfuric acid. After removal of the amine sulfonate, the residual liquid, containing any unreacted amine and the diluted acid, is recycled to complete utilization of the amine. The dilute sulfuric acid can be re-concentrated by removal of the water and the addition of oleum (30% or 60%). In this manner, complete utilization of the starting amine is achieved and the excess of acid is constantly reconstituted and recycled. Also, the distilled water containing a small amount of $H_2SO_4$ is utilized for the cooling diluent used to precipitate the amine sulfonate and then goes into reconstituting the acid by the addition of oleum.

This process is economically viable for the preparation of all the above amine sulfonates, many of which are required in tonnage lots. The reactions are conducted in the liquid medium, and primarily in the dissolved state thus avoiding conditions of local overheating, common in dry state reactions, with concomitant formation of colored impurities.

The products resulting from the reactions of this invention are of such good color that the usual carbon decolorization steps utilized heretofore can be omitted. In addition, because of the inherent simplicity of material handling in the liquid state, the invention leads itself to simple batch or continuous processing in the usual glass-lined reactors.

As the exotherm of the amine sulfate formation is of such magnitude, very little energy is required for control of the further reactions of re-arrangement, dilution reconstitution and recycling. In fact, the complete process would require no energy addition if sufficient heat storage and recycling is available for the energy removed during the cooling and dilution steps.

Of the amine sulfonates usefully prepared by the process of this invention, sulfanilic acid (SA) is economically one of the most important, as it is required in very large amounts for dyestuff production, e.g. the fluorescent brightening agents (Tinopal) used in paper-making, textiles and in laundry detergents. The invention will be more particularly described and its parameters outlined in connection with the laboratory preparation and large scale manufacturer of sulfanilic acid:

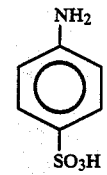

This invention, with regards to this amine is a process for the manufacture of sulfanilic acid from the reaction of aniline with sulfuric acid which comprises the steps of adding aniline to concentrated sulfuric acid (93+%) in the presence of an excess of sulfuric acid, equilibrated to provide a solvent sufficient for the reactants and the resultant reactant products and sufficient to adjust the reaction mixture temperature, resulting from the initial reaction exotherm forming the amine sulfate to between the rearrangement temperature for sulfonate formation and the decomposition temperature of the sulfanilic acid; and then distilling from said so heated mixture the water formed as a concomitant reaction product.

In the preparation of sulfanilic acid in the sulfuric acid solvent according to this invention it is noted that the reaction does not proceed simply according to the sequence Equations 1-2 but rather according to Equations III-VI.

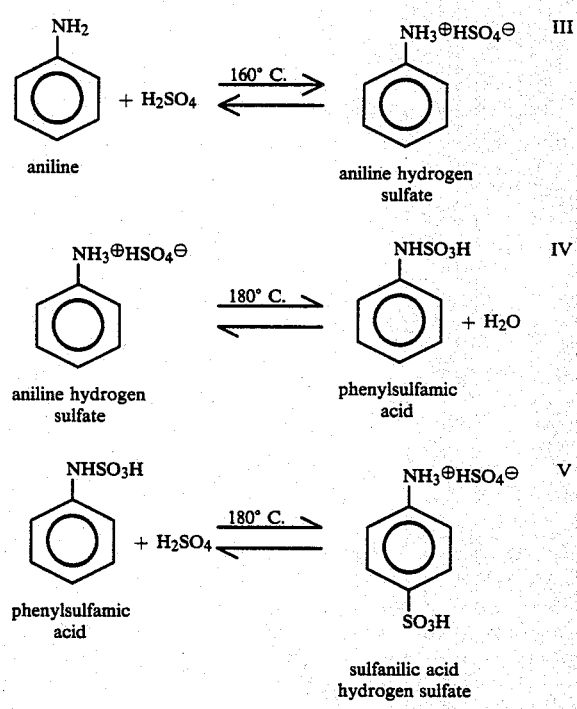

-continued

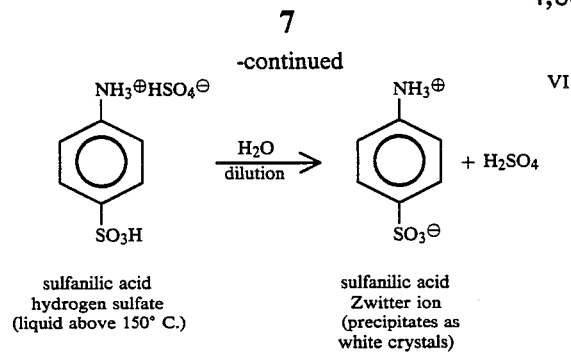

sulfanilic acid hydrogen sulfate (liquid above 150° C.)

sulfanilic acid Zwitter ion (precipitates as white crystals)

This four-stage reaction sequence provides purity control and minimizes colored by-product formation. The existance of the equilibrium stage (Equations III–V) has been shown by dissolving pure sulfanilic acid in sulfuric acid. This resulting solution assays at only 85% sulfanilic acid and contains 15% of an intermediate postulated as Phenyl Sulfamic Acid. Recycling results in 100% conversion of this intermediate to sulfanilic acid.

In this sulfanilic acid process, the invention requires that the molar ratio of aniline to sulfuric acid, as equilibrated reactant and medium is in the range 1:2.0 to 1:2.5. Beyond this range the reaction proceeds poorly. Below the lower end of the range the reaction mass becomes less fluid and longer hold times in both continuous and batch reactors are required. Above the higher end of the range, sulfanilic acid yields are lowered and recycling becomes excessive. Within this range the overall reactions are conducted at a temperature in the range 180°–230° C. At this temperature the water formed during the second stage (Equation IV) is distilled from the reactor vessel. The water should be removed or its presence will slow the reaction rates to impermissable levels.

This distilled water containing less than 2% $H_2SO_4$, is collected and utilized in the steps described below for the novel isolation of the sulfanilic acid (Equation VI) and recycling of any untransformed material.

In further aspects of this invention are included the recovery by separation of the sulfanilic acid formed in the reaction mixture which includes the steps of cooling the reaction mixtures from the reaction range of 180°–230° C. and then diluting the cooled mixture with the collected distilled water until the sulfuric acid concentration is reduced to the point where the sulfanilic acid forms a Zwitterion, insoluble in the diluted mixture (Equation VI). The mixture is cooled below about 130° C. The sulfuric acid concentration in the mixture, conducive to the formation of the insoluble Zwitter-ion, is below 70% and as low as 0% $H_2SO_4$. Under these conditions substantially all of sulfanilic acid is precipitated from solution. Any incompletely converted aniline products remain dissolved in the liquid. The sulfanilic acid, in the Zwitterion form, is recovered by separation means such as by filters or by centrifuge. The filtrate, containing the incompletely converted aniline products, is recycled to the main reaction by raising the sulfuric acid concentration and adding additional aniline.

The facile isolation of sulfanilic acid from the molten reaction mass simply by dilution with water is an important feature of this invention. That the sulfanilic acid hydrogen sulfate exists in strong acid ($\geq 70\%$ $H_2SO_4$) and is molten at the reaction temperature allowing good mixing and heat transfer was not expected or anticipated. It is largely responsible for allowing moderate reaction conditions that result in good product quality with light color. Addition of water to the reaction mass lowers the acidity sufficiently that the sulfanilic acid is no longer protonated and precipitates as the insoluble Zwitterion and is easily and efficiently collected by filtration.

The $H_2SO_4$ reconcentration is preferably achieved by adding 30 or 60% oleum ($H_2SO_4+SO_3$). The combination of the reconcentrated acid and recycled incompletely converted aniline products with the newly added aniline restarts the initial reaction of Equations III–V.

This invention, including the above discussed aspects can be carried out in a set of reactors wherein the feed, reaction, dilution and recycling are arranged to be continuous or the same steps can be successively performed in successive batches in appropriate vessels.

The separated sulfanilic acid should be washed with the water distilled from the rearrangement reaction (Equation IV) to remove any adhering acid and unconverted products from the desired precipitated sulfanilic acid. In practice, the sulfanilic acid is thus recovered in 97–99% purity as blue to white powder (Garner color $\leq 1$). The wash waters are then recycled.

In the preferred practice of this invention, the sulfuric acid and aniline are reacted, the sulfuric acid being present in the reaction mixture in the aniline: sulfuric acid ratio in the range of 1:2.0 to 1:2.5. The sulfuric acid initially is from 93 to 98% commercial sulfuric acid. Subsequently, the acid is derived from the recycled filtrate.

The filtrate has an acid concentration of from 30 to 75% $H_2SO_4$, preferably about 70%. This is concentrated by heating to distill off the excess water to reconcentrate the acid content to about 95–98%. Oleum, 30 to 60% can also be used to raise the $H_2SO_4$ concentration in the filtrate to about 93 to 98%. The recycled acid and the fresh acid are mixed to provide a reaction mixture proportioned in the aforesaid ratio with regard to the aniline feed.

As outlined earlier, sulfanilic acid and various intermdiates are in equilibrium (equations III–VI). The equilibrium is directed by the concentration of sulfuric acid in the reaction mixture. When an insufficient excess is present, insufficient phenyl sulfamic acid forms. As this is the intermediate for the conversion to form sulfanilic acid, the yield per pass through the reactor is reduced. In the presence of an excess of acid, the equilibrium is shifted toward the formation of phenyl sulfamic acid; thus also reducing the sulfanilic acid yield.

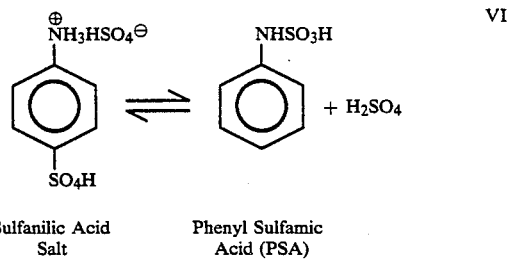

Sulfanilic Acid Salt

Phenyl Sulfamic Acid (PSA)

The equilibrium existing between sulfanilic acid and its hydrogen sulfate salt and/or phenylsulfamic acid is at a maximum with respect to sulfanilic acid formation (about 82–85% sulfanilic acid) when the reaction mixture excess $H_2SO_4$ content is one molar. While in the overall process of this invention the conversion of aniline can be 100%, the sulfanilic acid yield is limited by the equilibrium of equation VI (supra).

The postulated phenyl sulfamic acid in the filtrate is recycled to the initial feed and is converted to sulfanilic acid in the subsequent passes. Overall in the continuous process with recycle filtrate feeds, substantially complete conversion of aniline to sulfanilic acid is achieved in a uniform manner with less than 2% orthanilic and metanilic acids as impurities. If the molar excess of $H_2SO_4$ is kept below 2.5 with respect to aniline, virtually no disulfonic acids are formed.

The invention will be more specifically described in the below appended examples showing laboratory scale continuous and batch mode practice of the invention and plant scale examples in the continuous and batch modes. These examples will be illustrated by the drawing showing figuratively the following schematic flow diagrams wherein.

Figure 1:
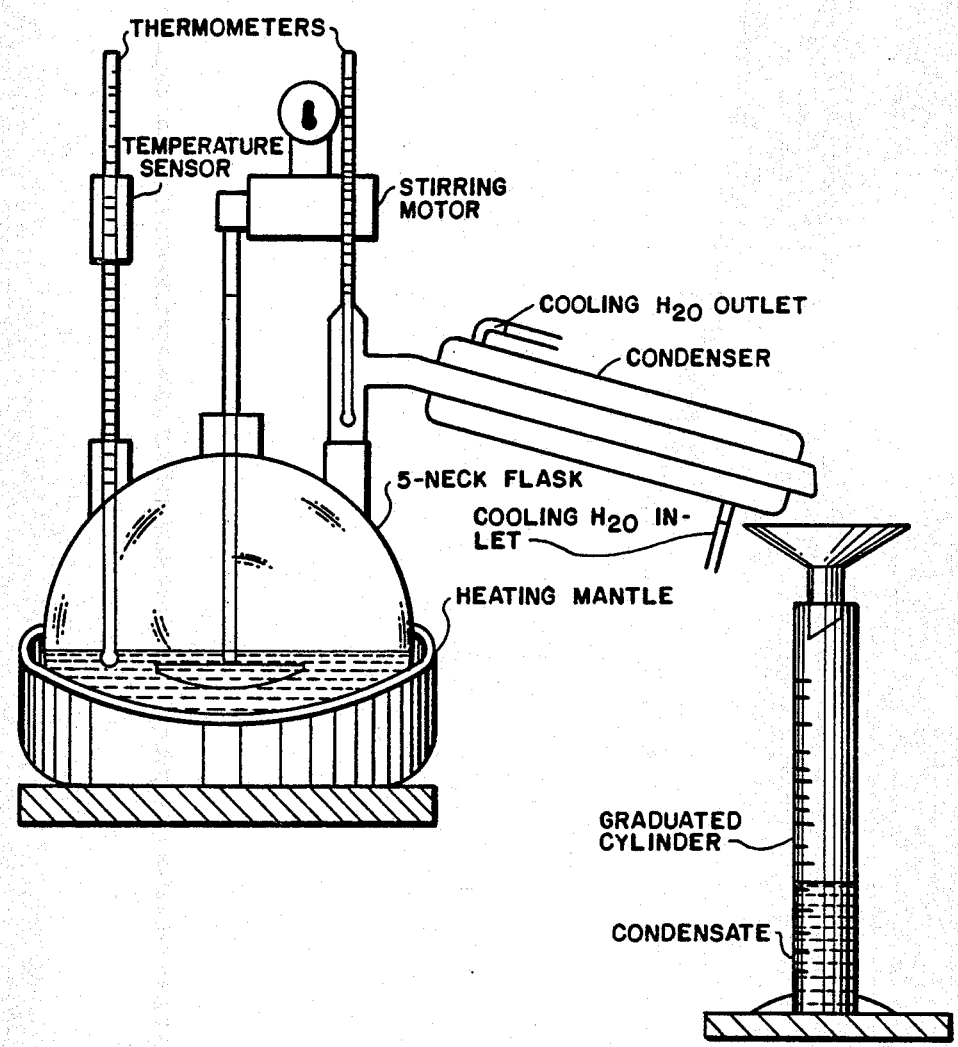
FIG. 1 shows a lab-scale batch reactor used as the reactor in the batch scale process of Example 1.

The below appended examples are intended to illustrate this invention as practiced in the laboratory and in the plant by presently preferred schemes. Except as specifically required by the parameters of this invention all materials and conditions described therein are all merely illustrative. All art-recognized equivalents thereof are intended.

Further, while the appended examples are directed to the economically most important sulfonated amine, sulfanilic acid, this invention is applicable to the economic production in substantially pure form of many sulfonated aromatic amines.* The required differences are the use of appropriate components and rearrangement termperatures. The molar ratio of sulfuric acid to aniline will have to be adjusted, depending on the solubility of the specific intermediates and specific products in the excess sulfuric acid and the specific exotherms of the reactions. These rearrangement temperatures are well-known and are listed in Table 1 below showing the the starting aromatic amine and the respective amine sulfonate product.

*The same procedure can be used to make other sulfonated aromatic amines.

TABLE 1

| Starting Material | Rearrangement Temperature °C. | Product |
|---|---|---|
| aniline (NH₂) | 175° | sulfanilic acid (NH₂, SO₃H para) |
| o-toluidine (CH₃, NH₂ ortho) | 235 | (CH₃, NH₂ with HO₃S) |
| p-toluidine (CH₃, NH₂ para) | 255 | (CH₃, NH₂ para with HO₃S) |
| m-toluidine (CH₃, NH₂ meta) | 160 | (CH₃, NH₂, SO₃H) |
| o-chloroaniline (NH₂, Cl ortho) | 230 | (NH₂, Cl, SO₃H) |
| p-phenetidine (OC₂H₅, NH₂ para) | 175 | (OC₂H₅, NH₂, SO₃H) |

EXAMPLE 1

Lab- Batch mode

A one liter round bottom reactor fitted with a water-cooled condenser was charged with 200 gm of 98% $H_2SO_4$. With continuous agitation, 93 gm of aniline was introduced with caution from a dropping funnel over a 20 minute period. The reaction was exothermic and heated the mixture to about 180°–200° C. The heating was continued until 18 gm of water distilled and was collected from the condenser. The reaction mass was allowed to cool to between 80°–90° C. and 24 gm cold water and 18 g of the distillate was added to reduce the remaining acid concentration to about 70% $H_2SO_4$ and the resulting mixture was cooled by an ice bath to about 30° C.

The cooled contents of the flask were filtered on a Buchner funnel. The cake was washed with 15 gm water. The cake consisted of 137 gms of sulfanilic acid. This is an in-hand yield of 77%. The product had an excellent color (<1.0 Gardner). Checking of the filtrate and wash water indicated a total sulfanilic acid yield of 83% (based on aniline). The combined filtrate and wash water were then concentrated by heating under vacuum to remove most of the water. This reconcentrated material was recycled as a component and as a portion of the acid. In subsequent batches with recycled acid and partially converted aniline-derived intermediates 98+% conversion of the aniline to sulfanilic acid was obtained.

EXAMPLE 2

Lab - Continuous Mode

Figure 2:
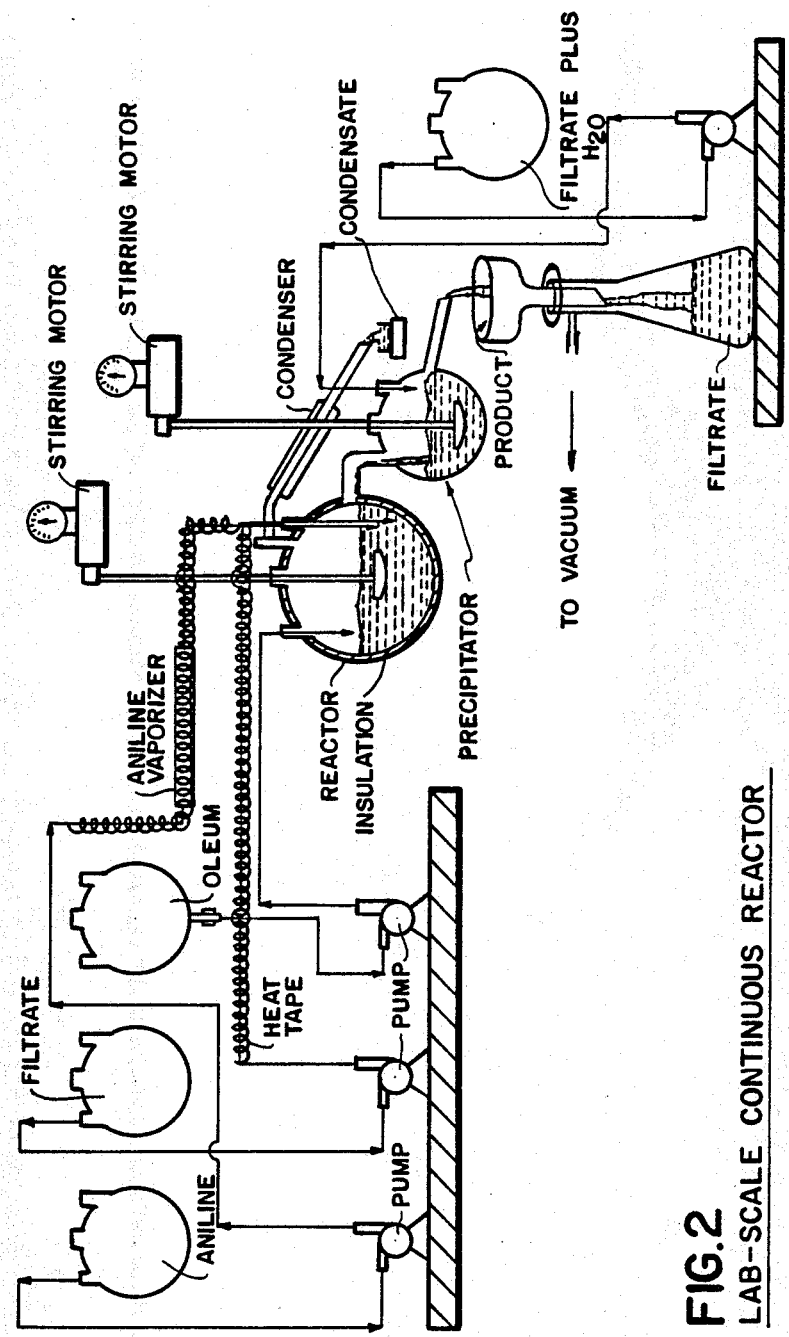
FIG. 2 shows a lab-scale continuous reactor flow diagram used in the continuous mode process of Example 2.

The apparatus of FIG. 2 is utilized.

The 3000 ml well-insulated, side-outlet reactor, fitted with thermometers and agitators, dropping funnels and inlets for heated aniline vapors and acid feeds was charged with 950 gm of 98% $H_2SO_4$. The agitator was started and 445 gm aniline was slowly added over 30 minutes by dropping funnel. The exothermic reaction heated the mixture in the flask, with some supplementary heat, to about 200° C. The temperature was maintained for about 45 minutes and the supplemental heat sources were turned off. The aniline vaporizer line was heated to about 200° C., the filtrate feed line was heated to 85° C. and the filtrate *(Note) flow into the reactor was started at about 6.1 gm/minute. The oleum line was activated at a feed rate of 4.2 gm/minute of 30% oleum (at ambient temperature). Then the aniline flow through the vaporizer (b.p. 186° C.) at 4 gm/min. was started. The aniline vapors at about 200° C. were introduced below the surface of the mixture in the reactor.

The flow of the filtrate/water mixture to the precipitator (FIG. 2) was started at 12.0 gm min. The agitator was turned on. The first 100 gm of precipitate overflow was removed and then the Buchner funnel was placed under the overflow outlet and the precipitated sulfanilic acid was filtered.

The filtrate was tranferred to the filtrate holding vessel for recycling to the reactor.

*Note: Initially, until sufficient filtrate for recycling is obtained, an artificial filtrate should be used. It is prepared as follows: To a 500 ml beaker in an ice bath is charged 71.1 gm of 98% $H_2SO_4$. The acid is cooled and 8.6 gm of aniline is slowly introduced with stirring (Exothermic Reaction). While stirring and cooling is continued 18.7 gm water is added (Exothermic Reaction). Finally 1.5 gm sulfanilic acid is dissolved in the mixture. The mixture separates into two phases at room temperature and must be heated to transfer to other vessels.

EXAMPLE 3

Plant scale - continuous mode

Figure 3:
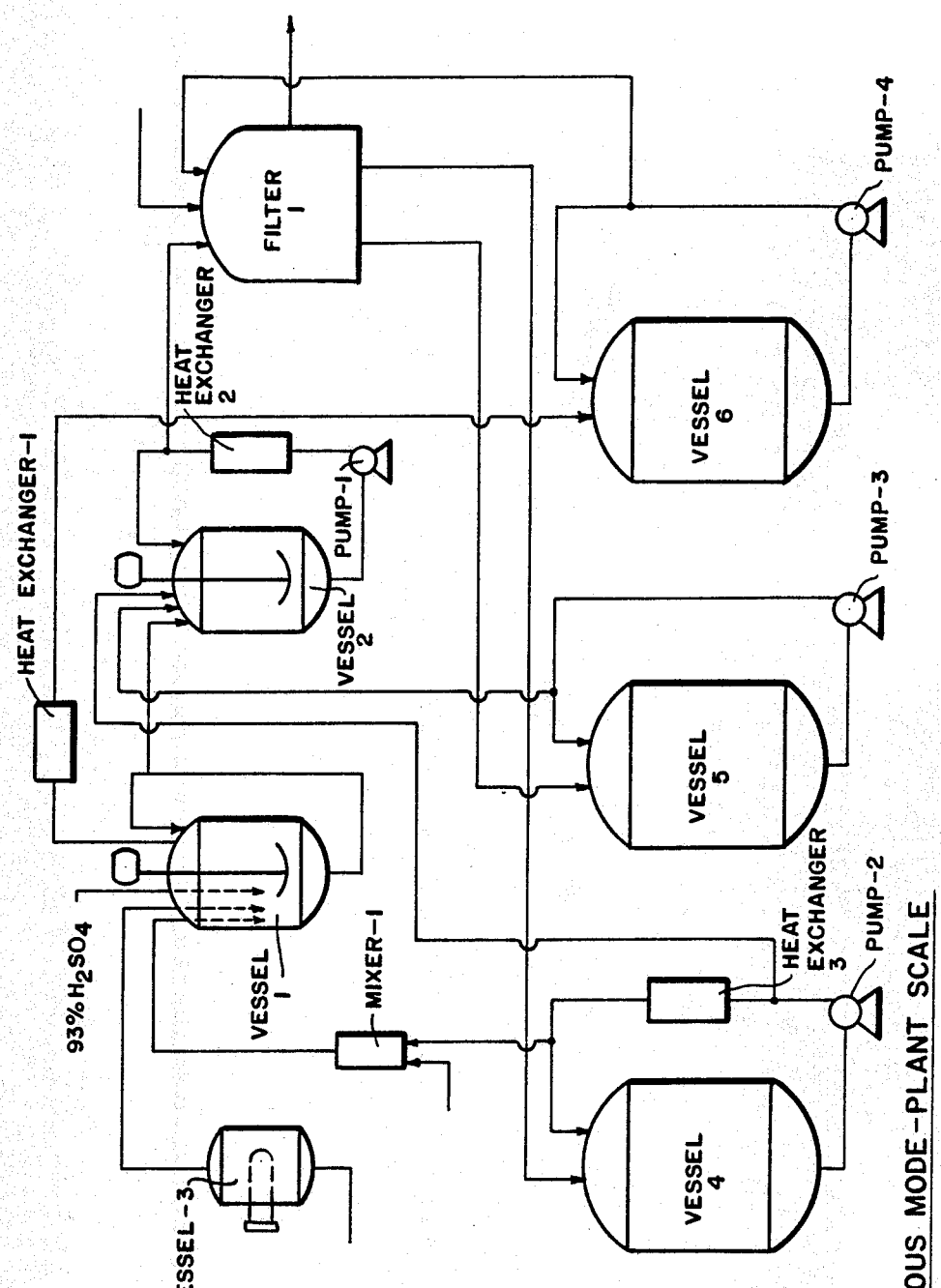
FIG. 3 shows a continuous mode layout for plant operation of the process of this invention as described in Example 3.

The process of this example was carried out in the apparatus of FIG. 3 wherein V-1, the reactor is a 100 gallon glass-lined vessel, jacketed, well-insulated, fitted with water-cooling and steam-heating means, sub-surface reactant feeds and capable of acid-resistance at 220° C. V-2, the crystallizer is a 100 gallon glass-lined steel vessel, jacketed and water-cooled to maintain a steady-state temperature 50° C. V-3, the aniline vaporizer, is a 25 gallon vessel with a submerged, heating element capable of vaporizing and heating the aniline vapors to about 200° C. V-4, V-5 and V-6 are 500 gallon acid-resistant storage vessels. HE-1, HE-2 and HE-3 are heat exchangers, fabricated from graphite, Teflon- or glass-lined steel for condensation and cooling of water vapor. F-1 is a filter but can be replaced by a centrifuge capable of handling the highly acidic liquids at 50° C. M-1 is a static mixer with Teflon-lined stators and rotor. P-1 is a teflon-lined slurry pump for transfer of the sulfanilic acid slurry. P-2 is a filtrate pump, Teflon-lined to handle the acidic filtrate. P-3 and P-4 are the wash-water and condensate pumps respectively.

In the practice of the invention in the continuous mode, the following start-up procedure is used.

Charge 110 gal. of 75% $H_2SO_4$ (1200 lbs of 93% $H_2SO_4$ mixed with 290 lbs of $H_2O$) to storage vessel V-4. Charge 90 gal. of 75 wt % of $H_2SO_4$ to crystallizer V-2. Charge 130 gal of 45 wt % $H_2SO_4$ to storage vessel V-5 and 120 gal of $H_2O$ to storage vessel V-6. Charge 45 gal of 93 wt % $H_2SO_4$ to reactor, V-1, and start the agitator therein while opening the condenser vent. Slowly charge 37 gal of liquid aniline to reactor V-1 (EXOTHERMIC REACTION). The temperature in reactor V-1 must be controlled below 220° C. by controlling the rate of aniline feed. The temperature is maintained in the range of 205°–220° C. The dwell time of the mixture in the reactor at the lower temperature, in the range of 205° C.–210° C. is about 60 minutes and at the upper temperature limit is 25 minutes. If the temperature should fall below about 180° C., oleum is added to raise the temperature. When the above indicated dwell time is completed, the oleum, filtrate and vaporized aniline flows are started and all pumps, valves etc, are opened and the system is allowed to commence steady state operation as follows:

Aniline (from storage) is fed to aniline vaporizer V-3 where it is vaporized and then introduced into reactor V-1 through a sub-surface inlet line.

Oleum 30% from storage is mixed with preheated filtrate from storage vessel V-4 in mixer M-1. The resulting mixture, proportioned to two moles $H_2SO_4$, is also fed to reactor V-1 and introduced through a sub-surface inlet line. The heat of vaporization of aniline, the heat of mixing oleum with filtrate, the latent heat of the filtrate stream and the heat of reaction between aniline and $H_2SO_4$ provide the heat required for aniline sulfonation. The preferred steady state temperature is 220° C.

As the sulfonation reaction proceeds, water (containing less than 4% $H_2SO_4$) distills from the reaction mass and is vented via overhead line to heat exchanger HE-1 where it is condensed, cooled to 50° C. and sent to tank V-6 for storage. The reaction mass, after a hold-up time of approximately 108 minutes, flows by gravity from reactor V-1 to crystallizer V-2. The recycled intermediate, postulated as phenyl sulfamate, present in the recycled filtrate stream, allows for virtually 100% conversion of aniline to sulfanilic acid in reactor V-1.

In crystallizer V-2, the reaction mass at 220° C. is mixed with recycled filtrate and wash liquid from storage tank V-5. The reduction of acidity in the reaction mass, by the addition of water contained in the filtrate and wash liquid to the reaction mass, causes the sulfanilic acid to be precipitated in the crystallizer. The resulting sulfanilic acid slurry is cooled to 50° C. in crystallizer V-2 with the aid of external heat exchanger HE-2. The cooled slurry is then pumped to filter F-1 for separation from the liquids.

The separated sulfanilic acid is recovered from filter F-1 and is washed with the condensate from storage tank V-6 and plant water. The recovered wash liquid is pumped to tank V-6 for storage prior to recycling as coolant in the crystallizer.

The filtrate is collected from filter F-1 (or if a centrifuge is used from such a separator) and is stored in storage tank V-4 at 50° C. and from which it is recycled to mixer M-1. It is there mixed with 30% oleum to bring up to 2 molar $H_2SO_4$ ratio with respect to aniline.

After steady state operation for six hours, the washed sulfanilic acid was sampled and assayed. It was of 99+% purity and had a superior color, Gardner<1. The overall material analysis indicated tht the sulfanilic acid yield based on aniline feed was 98+%. This was due to efficient conversion of the incompletely reacted intermediates, (postulated as phenyl sulfamate,) in the filtrate to sulfanilic acid upon recycling of the filtrate.

The process of this example is ecologically advantageous as all liquid streams are recycled and substantially no effluent is produced. Sulfanilic acid decomposes slowly at high temperatures in concentrted $H_2SO_4$. Trace amounts of $SO_x$ and $NO_x$ from such decomposition have been noted. Reactor V-1 and heat exchanger HE-1 are thus, for ecological considerations, vented to a scrubber system capable of removing these gases. It should be noted that this decomposition is so small that no measurable loss in yield could be detected in several test runs.

EXAMPLE 4

Plant Scale - Batch Mode.

Figure 4:
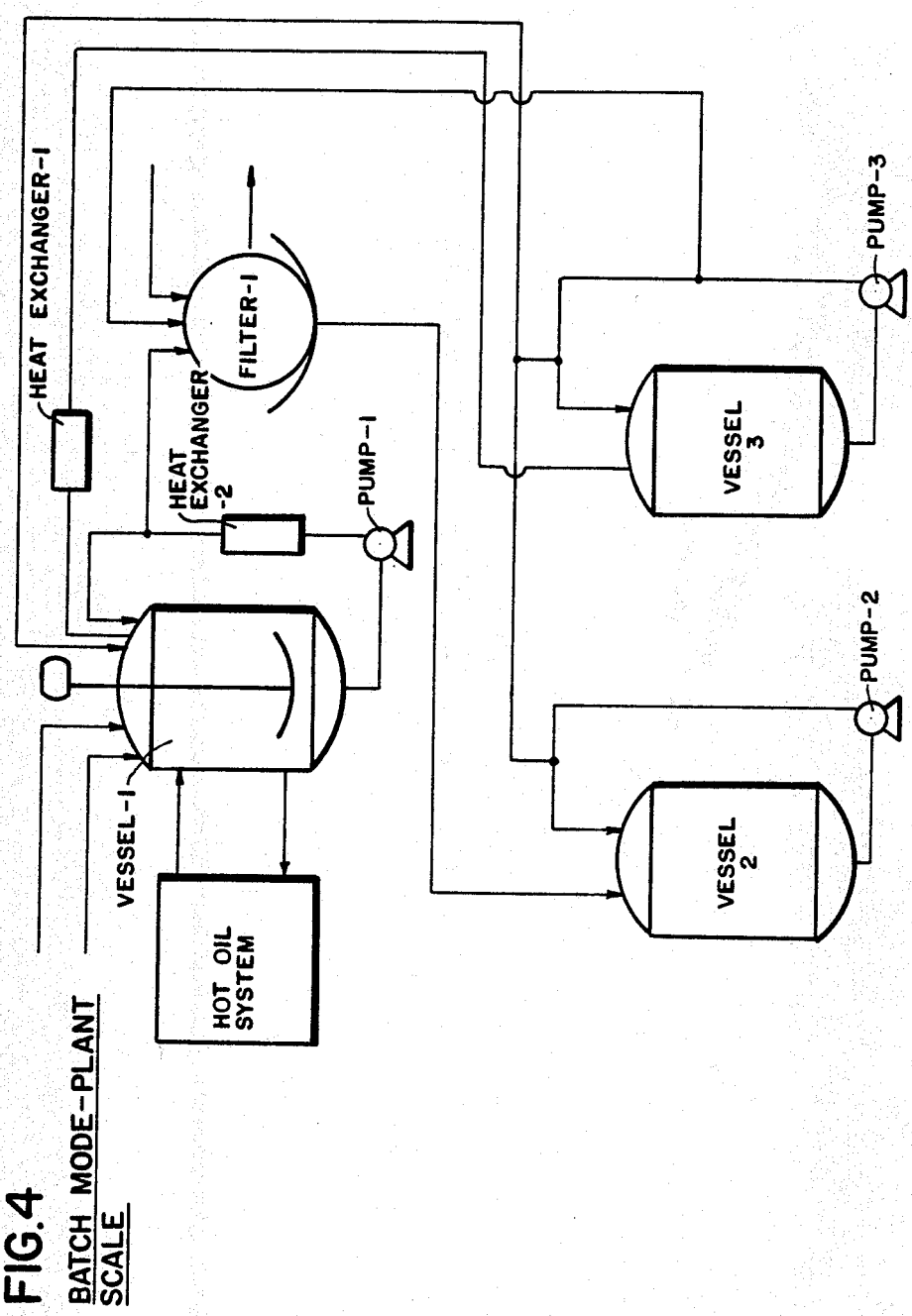
FIG. 4 shows a plant scale batch mode layout for plant operation according to Example 4 of the process of this invention.

This mode of manufacture is carried out in the apparatus and process scheme layout shown in FIG. 4 where the reaction and crystallization take place in reactor V'-1, a 1500 gallon, glass-lined steel vesel, equipped with an agitator and jacketed for heating and cooling by an external heat transfer system. The reactor V'-3 of 1000 gal. capacity serving as filtrate and condensate storage, via respective pumps. P'-2 serving to transfer filtrate and pump P'-3 for condensate transfer. Heat exchanger HE'-1 is positioned in the overhead line between reactor V'-1 and condensate storage vessel. Heat exchanger HE'-2 circulates the slurry from the bottom of reactor V'-1 for cooling the contents thereof to control and insure precipatation. The slurry circulated through the exchanger HE'-2 is moved by pump P'-1 which also serves to transfer the slurry from reactor V'-1 to filter F'-1 and the filtrate therefrom to storage vessel V'-2.

The batch mode aspect of this invention consists of an initial start-up phase followed by the normal operating procedure. The start-up consists in charging 930 gal. of 50% $H_2SO_4$ into filtrate vessel V'-2 and 600 gal. of water into vessel V'-3. Reactor V'-1 is charged with 403 gal. of 93% $H_2SO_4$ and the agitation is started.

The condenser vent leading to heat exchanger HE'-1 and thence to condensate tank V'-3 is opened. Aniline, 320 gal., is very slowly charged into reactor V'-1. This is an exothermic reaction and must be closely monitored to below 180° C. The aniline flow must be controlled to prevent aniline vapors from reacting with the $H_2SO_4$ vapors as such a vapor phase reaction causes dianiline sulfate to form from the aniline hydrogen sulfate. When all the aniline has been added, reaction vessel V'-1 and its contents are heated (by hot oil) to 200° C. and maintained at 200° C. until about 62 gal. of water (containing less than 2% $H_2SO_4$) distills. This takes about 2 hours. When the distillation is completed, the reactor V'-1 is cooled until at a temperature of about 110° C., 350 gal. of 50% $H_2SO_4$ from filtrate storage V'-2 is added. Cooling is continued until at about 100° C. about 335 gal. of water from condensate storage tank V'-3 is added to the reactor and cooling is continued until the contents thereof is cooled to about 50° C. At that temperature the slurry contents of the reactor V'-1 is pumped to filter F'-1 for filtration. The filtrate from the filter F'-1 is pumped to filtrate storage vessel V'-2 for recycling. The filter cake on filter F'-1 is washed with 234 gal. of $H_2O$. This wash water is also pumped to storage vessel V'-2 for recycling. The filter cake, essentially pure sulfanilic acid, is dried and readied for further processing as an intermediate. The start-up phase is now complete and Normal Operation Procedure commences as follows: Reactor V'-1 is charged with 180 gal. of 93% $H_2SO_4$ and 506 gal. of filtrate from filtrate storage vessel V'-2. Aniline, 273 gal. is slowly charged to reactor V'-1. This reaction is exothermic and the temperature should be monitored and controlled by the rate of aniline addition to about 130° C., the boiling point of the filtrate, thus preventing the above mentioned vapor reaction. When all the aniline has been added, the heating of the reactor is started. At 130° C. the filtrate begins to boil. The condensate is cooled and pumped to condensate storage tank V'-3. As the distillate is removed the temperature in the reactor V'-1 increases. The distillation is continued until the temperature in reactor V'-1 reaches 200°–205° C. and the temperature is maintained within this range for about one and a half hours. A total of 309 gal. of distillate is produced from the filtrate concentration and the reaction.

At this point reactor V'-1 is cooled until the contents reach 110° C. at which temperature 424 gal. of filtrate from filtrate storage tank V'-2 is introduced into the reactor V'-1. Cooling is continued to 100° C. at which point 228 gal. of cooled $H_2O$ (condensate) from condensate tank V'-3 is added to the reactor. When the contents of the reactor V'-1 reach 50° C. the resulting slurry is pumped to filter F'-1 for separation of the sulfanilic acid from the filtrate. The filtrate from F'-1 is pumped to V'-2 for recycling. The filter cake on F'-1 is first washed with 80 gal. of condensate from storage tank V'-3 and then with 15.4 gal. of water (external source). The wash water is added to the filtrate tank V'-2 for storage and recycling. The wet cake is ready for direct use in other processes. It has a Gardner color of less than 1 (in 17% solution).

After about twelve recycles the filtrate should be reworked to prevent discolorization of the product from over-worked incompletely reacted intermediate and to reduce effluent from discarded overworked filtrate.

The reworking should procede as follows:

The entire contents of filtrate storage tank V'-2, approximately 930 gal., is pumped to the reactor V'-1. The agitator is started and the vent to the condenser HF'-1 is opened. Reactor V'-1 and contents are heated. At 130° C. the filtrate will begin to boil. The distillate is condensed, cooled at 50° C. and pumped to condensate storage tank V'-3. The distillation is continued until the temperature of the reactor V'-1 contents reaches 200° C.

The contents are maintained at 200° C. for about 1½ hours or until about 420 gal. of distillate comes over. This amount results first from the boiling filtrate and then from the reaction itself. At that point cooling of the reactor V-1 contents is started. At 100° C., 480 gal. of water (condensate) from V'-3 at less than 50° C. is added and with external cooling to further cool the reactor contents to about 30° C. At this point the contents of the reactor V'-1 is transferred to F'-1 for separation of the solid from the liquid.

Approximately 1200 lbs. of sulfanilic acid is recovered at the filter. The wet cake is washed. The filtrate and wash streams are sent to effluent treatment. These streams represent a total loss of about 55 lbs. of sulfanilic acid and about 120 lbs. of aniline, as converted intermediates. This is a small amount of discard after about 12 batches representing a total of about 55,000 lbs of sulfanilic acid.

As is common, where oleum is economically available it may be used to reinforce the strength of the sulfuric acid in the filtrate and to reinforce the sulfuric acid in the initiation stage of the batch mode.

The invention herein is meant to be limited in its scope only by the specific metes and bounds of the appended claims.

What is claimed is:

1. In a process for the production of a sulfonated aromatic amine of the formula:

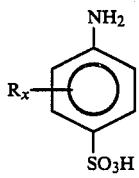

where R is H, CH$_3$, C$_2$H$_5$, halogen or

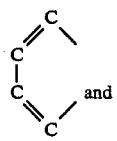

and x is the integer 0 to 2; which comprises the steps of reacting an aromatic amine of the formula

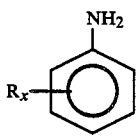

with concentrated sulfuric acid to form an intermediate aromatic amine hydrogen sulfate of the formula

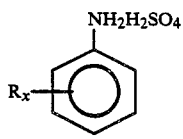

then heating this amine sulfate to cause rearrangement thereof with the formation of a sulfonate group and the elimination of a mole of water, the orientation of said sulfonate group being para- or ortho- to the regenerated amine group;

wherein the improvement comprises adding said aromatic amine to said concentrated sulfuric acid in the presence of a sufficient excess of concentrated sulfuric acid so that the molar ratio of the amine to the sulfuric acid is 1:2.0 to 1:2.5, the amount and concentration of said sulfuric acid being selected so that the exotherm of the reaction of said amine with the sulfuric acid to form the amine sulfate will maintain the temperature of the reaction mixture between the rearrangement temperature for the amine hydrogen sulfate and the decomposition temperatures of said amine hydrogen sulfate and amine sulfonate; distilling and collecting from said reaction mixture the water formed during said sulfonate formation; then upon completion of said distillation, cooling said reaction mixture to below the rearrangement temperature; diluting said cooled mixture with water to reduce the acid concentration thereof, thus causing said aromatic amine sulfonate which is insoluble in such lower acid concentration to precipitate, separating and washing, with said distilled water, said precipitated amine sulfonate and collecting same, and recycling the resulting acid filtrate together with wash waters and any incompletely or unreacted amine to the initial reaction mixture after said filtrate is reconcentrated with oleum to concentrated H$_2$SO$_4$.

2. A process according to claim 1 wherein the aromatic amine is aniline.

3. A process according to claim 2 wherein the concentration and amount of sulfuric acid are chosen so as to provide a rearrangement temperature in the range of 180° C. to 230° C. and distilling of the water formed as a result of said reaction without additional heating or cooling.

4. A process according to claim 2 wherein the filtrate is reconcentrated to at least 93% H$_2$SO$_4$ by the addition of oleum.

5. The process according to claim 2 wherein the reaction mixture, upon reaction completion, is cooled to below 130° C. and diluted to a sulfuric acid content in the range 30–75% H$_2$SO$_4$ before filtration.

6. The process according to claim 5 wherein the mixture is diluted with water distilled from the initial reaction and/or recycled filtrate and wash waters.

* * * * *